(12) United States Patent
Tronnes et al.

(10) Patent No.: US 7,590,451 B2
(45) Date of Patent: Sep. 15, 2009

(54) AXIAL LEAD CONNECTOR FOR IMPLANTABLE MEDICAL DEVICES

(75) Inventors: Carole A. Tronnes, Stillwater, MN (US); Robert A. Munoz, Chandler, AZ (US); Alexander O. Lakanu, Brooklyn Park, MN (US); John M. Swoyer, Andover, MN (US); Greg A. Theis, Apple Valley, MN (US); Bryan J. Zart, Shakopee, MN (US); David J. DeSmet, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 415 days.

(21) Appl. No.: 11/263,526

(22) Filed: Oct. 31, 2005

(65) Prior Publication Data
US 2007/0100386 A1    May 3, 2007

(51) Int. Cl.
*A61N 1/365* (2006.01)
(52) U.S. Cl. ....................................................... 607/37
(58) Field of Classification Search ............... 607/36–38
See application file for complete search history.

(56) References Cited

U.S. PATENT DOCUMENTS

| | | |
|---|---|---|
| 4,469,104 A | 9/1984 | Peers-Trevarton |
| 4,898,173 A | 2/1990 | Daglow et al. |
| 4,934,366 A | 6/1990 | Truex et al. |
| 4,934,367 A | 6/1990 | Daglow et al. |
| 5,012,807 A | 5/1991 | Stutz, Jr. |
| 5,070,605 A | 12/1991 | Daglow et al. |
| 5,257,622 A | 11/1993 | Hooper et al. |
| 5,413,595 A | 5/1995 | Stutz, Jr. |
| 5,669,790 A | 9/1997 | Carson et al. |
| 5,843,141 A | 12/1998 | Bischoff et al. |
| 6,006,135 A | 12/1999 | Kast et al. |
| 6,205,358 B1 | 3/2001 | Haeg et al. |
| 6,895,276 B2 | 5/2005 | Kast et al. |
| 7,070,455 B2 | 7/2006 | Balsells |
| 7,083,474 B1* | 8/2006 | Fleck et al. .................. 439/668 |
| 7,195,523 B2* | 3/2007 | Naviaux ...................... 439/827 |
| 2003/0073348 A1 | 4/2003 | Ries et al. |
| 2003/0163171 A1 | 8/2003 | Kast et al. |
| 2004/0122481 A1 | 6/2004 | Tidemand et al. |
| 2004/0260355 A1 | 12/2004 | Holleman et al. |
| 2005/0027326 A1 | 2/2005 | Ries et al. |
| 2005/0131481 A1 | 6/2005 | Ries et al. |
| 2005/0131483 A1 | 6/2005 | Zhao et al. |
| 2005/0222634 A1 | 10/2005 | Flickinger et al. |
| 2005/0245982 A1 | 11/2005 | Kast et al. |
| 2006/0004420 A1 | 1/2006 | Rossing et al. |

FOREIGN PATENT DOCUMENTS

| | | |
|---|---|---|
| EP | 0 339 877 | 11/1989 |
| WO | WO 00/64535 | 11/2000 |
| WO | WO 03/075414 | 9/2003 |
| WO | WO 2005/081927 | 9/2005 |

\* cited by examiner

*Primary Examiner*—George R Evanisko
*Assistant Examiner*—Amanda Patton
(74) *Attorney, Agent, or Firm*—Shumaker & Sieffert, P.A.

(57) ABSTRACT

An axial lead connector assembly for an implantable medical device (IMD) facilitates electrical connection between an implantable medical lead and circuitry contained within the housing of an IMD. A connector header defines an axial stack bore to receive an axial stack of in-line connector components. The connector components define a common lead bore to receive a proximal end of an implantable lead. The in-line stack of connector components may include seals, electrical connector elements, a strain relief, and a locking device, each of which defines a passage that forms part of the lead bore.

34 Claims, 10 Drawing Sheets

AXIAL LEAD CONNECTOR FOR IMPLANTABLE MEDICAL DEVICES

TECHNICAL FIELD

The invention relates to medical leads for implantable medical devices (IMDs) and, more particularly, to electrical connectors that facilitate electrical coupling between the medical leads and circuitry of the IMD.

BACKGROUND

In the medical field, leads are used with a wide variety of medical devices. For example, leads are commonly used with implantable stimulators that provide electrical stimulation. Electrical stimulation may be delivered to sacral, pudendal or other pelvic nerves within the pelvic floor of a patient to alleviate a variety of disorders such as urinary incontinence, fecal incontinence, constipation, sexual dysfunction, pelvic pain, or other pelvic floor disorders. Other applications include spinal cord stimulation, gastric stimulation and deep brain stimulation. The electrical stimulation is delivered via electrodes disposed at or near the distal ends of one or more leads. Leads may also be used with implantable cardiac pacemakers that provide therapeutic stimulation to the heart by delivering pacing, cardioversion or defibrillation pulses. In that case, the leads may position the electrodes with respect to various cardiac locations so that the pacemaker can deliver pulses to the appropriate locations. Leads may also be used for sensing purposes, or both sensing and stimulation purposes.

One challenge in implementing medical leads in a medical device is the electrical coupling between a lead and circuitry of the IMD. An IMD includes a housing that houses an implantable pulse generator (IPG) containing circuitry, and a connector module that couples the lead to the circuitry, either directly or via a lead extension. The connector module includes electrical contact structures for coupling the lead to circuitry within the housing of the IMD so that therapeutic simulation can be provided through the lead, or sensed conditions can be recorded by the circuitry. The connector module must ensure reliable electrical connections between the IMD circuitry and the lead, while also maintaining a sufficient seal between the connector module and the lead to avoid ingress of body fluids into the housing, and the possibility of electric shorting between electrodes. These requirements contribute to manufacturing complexity and cost, and can make the connection of the lead to the IMD difficult for the physician.

SUMMARY

In general, the invention is directed to an axial lead connector assembly for an implantable medical device (IMD). The lead connector assembly facilitates electrical connection between an implantable medical lead and circuitry contained within the housing of an IMD. A connector header defines an axial stack bore to receive an axial stack of in-line connector components. The connector components define a common lead bore to receive a proximal end of an implantable lead. The in-line stack of connector components may include seals, electrical connector elements, a strain relief, and a locking device, each of which defines a passage that forms part of the axial lead bore.

Electrically conductive connector elements are disposed within the axial stack bore at positions corresponding to positions of electrically conductive lead contacts carried at the proximal end of the lead. Each connector element couples one of the lead contacts to a conductor within the IMD housing. Each connector element may be integrated with, or adjacent to, a seal device that provides a fluid seal with respect to adjacent connector elements or the outside of the connector header. An annular strain relief member, mounted in an opening of the axial stack bore, retains the stack of components within the connector header, and receives the proximal end of the lead. The axial stack of connector components may be preassembled or pre-fitted for insertion into the axial stack bore as a unitary stack. Alternatively, the individual connector components may be inserted serially into the axial stack bore, e.g., one or more components inserted at time.

Each electrical connector element may provide an interference or friction fit to a respective contact on the lead, enhancing electrical coupling pressure. Seals may provide a similar interference or friction fit with the lead body. A locking device, such as a set screw assembly, exerts a lateral force against the lead such that the proximal end of the lead resists axial displacement under axial loading forces. The strain relief member may support the lead against bending forces. The locking device also may be electrically conductive and function as an electrical connector element for one of the contacts carried by the lead. In some embodiments, a single set screw assembly may be provided. The lead is coupled via the connector header to circuitry within the IMD housing to deliver electrical stimulation therapy or sense patient conditions.

In one embodiment, the invention provides an implantable medical device comprising a connector header defining a first axial bore, and a series of electrical connector elements and fluid seals arranged in an axial stack mounted within the first axial bore, wherein the axial stack defines a second axial bore that extends through the electrical connector elements and fluid seals to receive a proximal end of an implantable medical lead.

In another embodiment, the invention provides an implantable medical device comprising a connector header defining a first axial bore, and an axial stack of connector components within the first axial bore, wherein the axial stack defines a second axial bore extending through the components that receives a proximal end of an implantable medical lead, and wherein the components include electrical connector elements, fluid seals, a locking device that exerts a force to resist displacement of the lead, and a strain relief member.

In a further embodiment, the invention provides a method for assembling an electrical connector assembly for an implantable medical device comprising arranging a series of electrical connector elements and fluid seals in an axial stack, and inserting the axial stack into a first axial bore defined by a connector header, wherein the axial stack defines a second axial bore that extends through the electrical connector elements and fluid seals to receive a proximal end of an implantable medical lead.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
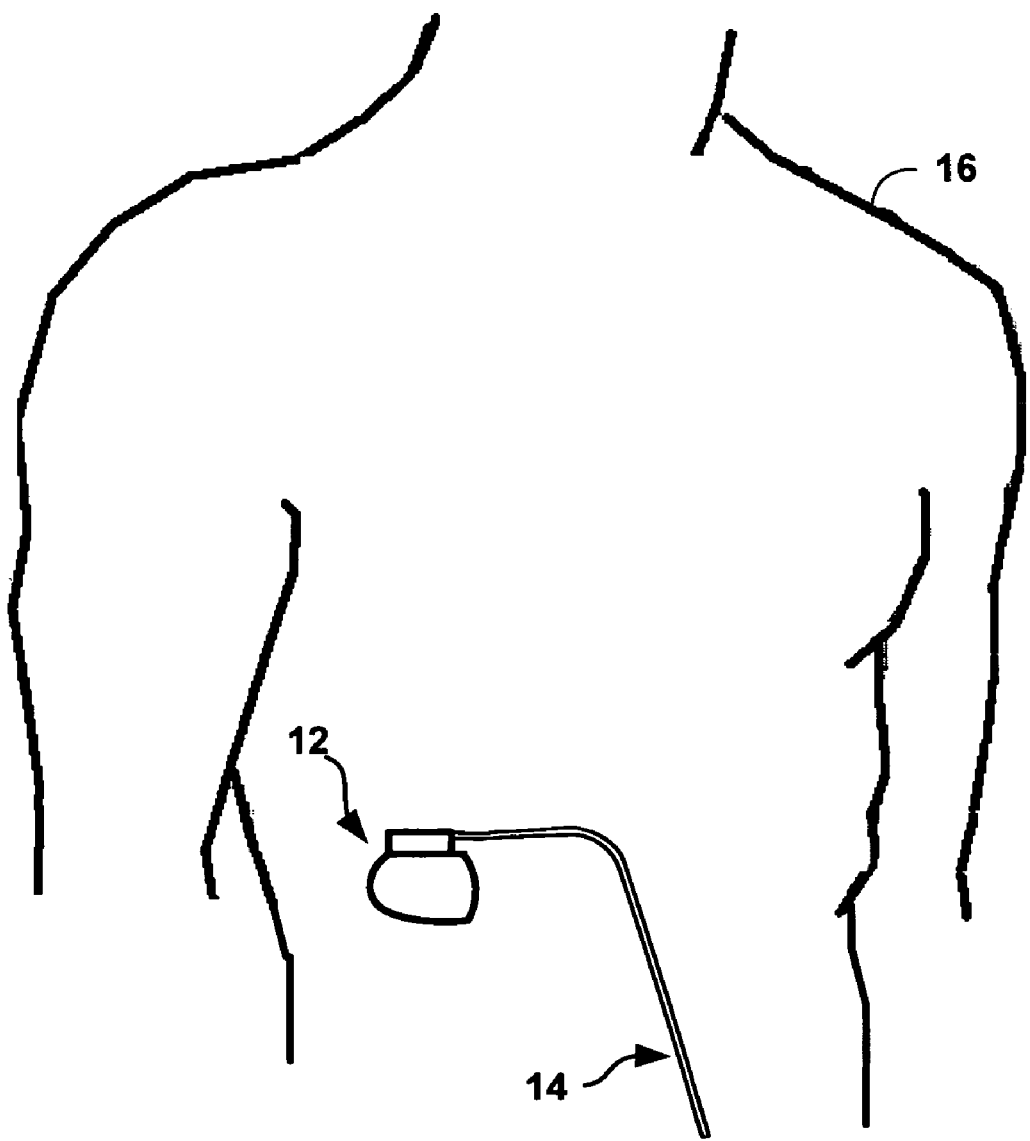
FIG. 1 is a block diagram illustrating an IMD with a lead implanted within a patient.

FIG. 1 is a block diagram illustrating an implantable medical device (IMD) 12 having a lead 14 implanted within patient 16. Lead 14 includes one or more electrodes (not shown in FIG. 1) at or near a distal end of the lead. As will be described, IMD 12 includes a lead connector assembly that facilitates electrical connection between lead 14 and circuitry contained within the housing of an IMD. In accordance with the invention, the lead connector assembly defines an axial stack bore to receive an axial stack of in-line connector components. The connector components together define a common lead bore to receive a proximal end of an implantable lead. The in-line stack of connector components may include seals, electrical connector elements, a strain relief, and one or more locking devices, each of which defines a passage that forms part of the axial lead bore.

A proximal end of lead 14 carries one or more electrical contacts that are coupled to respective electrodes via conductors within the body of the lead. IMD 12 may be an implantable stimulator that delivers electrical stimulation to nerve or muscle tissue within patient 16. For example, IMD 12 and lead 14 may be configured to deliver electrical stimulation to sacral, pudendal or other pelvic nerves within the pelvic floor of a patient to alleviate a variety of disorders such as urinary incontinence, fecal incontinence, constipation, sexual dysfunction, pelvic pain, or other pelvic floor disorders. Lead 14 is sized in diameter and length for any of a variety of nerve or tissue stimulation applications.

Alternatively, IMD 12 and lead 14 may be configured for spinal cord stimulation, e.g., for chronic pain, or gastric stimulation, e.g., for gastroparesis, obesity or other gastric disorders. As another example, implantable stimulator 12 may provide deep brain stimulation for alleviation of motion disorders, Parkinson's disease, epilepsy, or other neurological disorders. In those cases, lead 14 may be stereotactically probed into the brain to position electrodes for deep brain stimulation or into the spine for spinal stimulation.

As a further example, IMD 12 may take the form of an implantable cardiac pacemaker that provides therapeutic stimulation to the heart. Alternatively, IMD 12 may take the form of an implantable cardioverter or an implantable defibrillator, or an implantable cardiac pacemaker-cardioverter-defibrillator. IMD 12 may deliver pacing, cardioversion or defibrillation pulses to a patient via electrodes disposed on a distal end of lead 14. Accordingly, lead 14 may position electrodes with respect to various cardiac locations so that IMD 12 can deliver pulses to the appropriate locations.

As a further alternative, IMD 12 may correspond to a patient monitoring device that senses physiological parameters, or a device that integrates sending and electrical stimulation features. In those cases, lead 14 may include sensors disposed on distal ends of the respective lead for sensing patient conditions. The sensors may comprise electrodes, electrochemical sensors, pressure sensors, flow sensors, acoustic sensors, optical sensors, or the like. In many cases, IMD 12 may perform both sensing and stimulation functions. IMD 12 may correspond to any of a wide variety of medical devices that implement one or more leads and circuitry coupled to the leads to support stimulation, sensing, or both.

Figure 2:
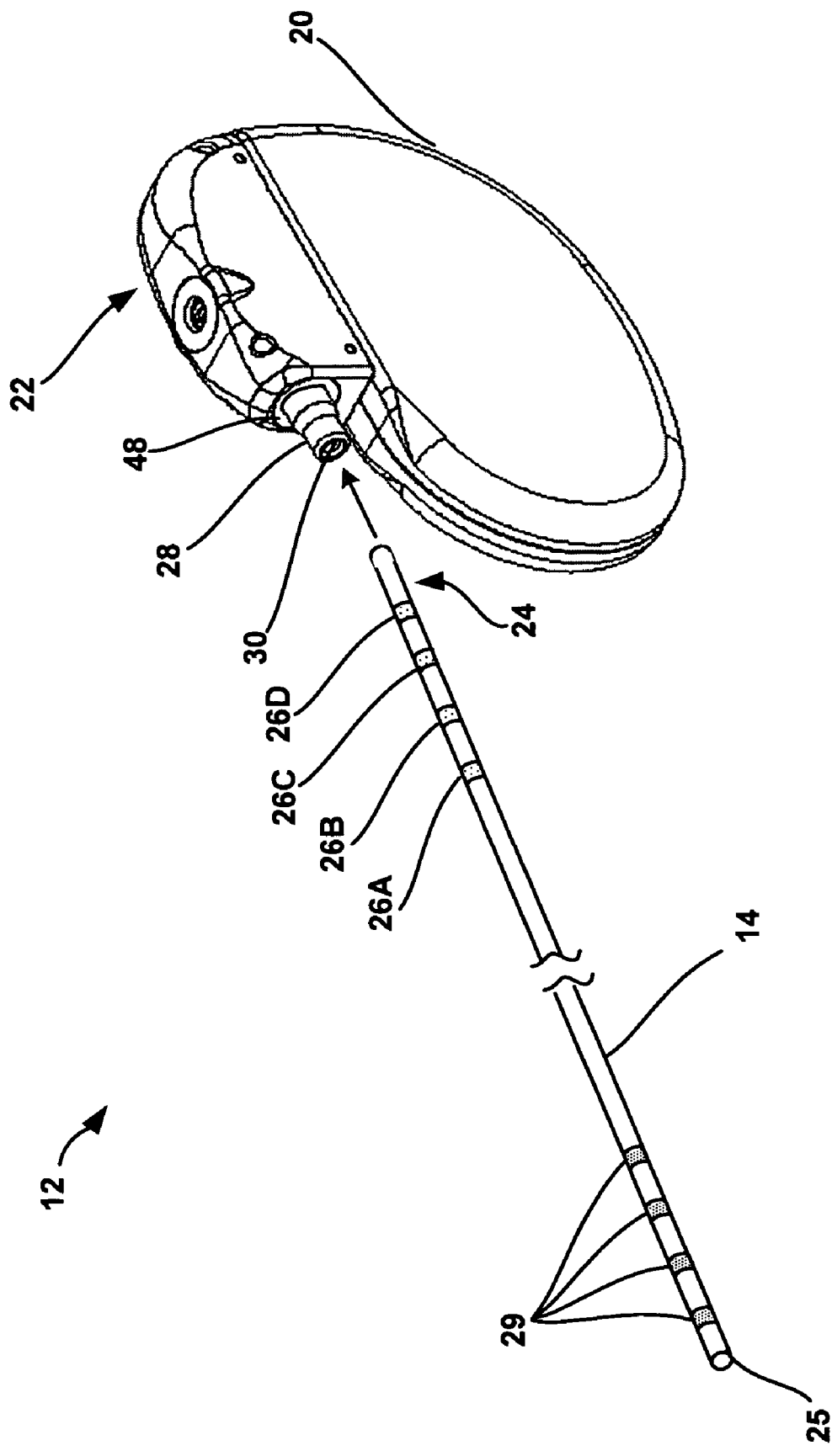
FIG. 2 is a perspective view of an exemplary IMD with an axial lead connector assembly in conjunction with a lead.

FIG. 2 is a perspective view of an exemplary IMD 12 that includes a lead 14. IMD 12 includes a housing 20 that houses IMD circuitry, including stimulation pulse generation circuitry, power generation circuitry, and telemetry circuitry. In some embodiments, IMD 12 additionally or alternatively may include sensing circuitry. IMD 12 is coupled to a lead 14 via an axial lead connector assembly 22 that receives a proximal end 24 of lead 14 to couple lead 14 to the circuitry in housing 20. Housing 20, sometimes referred to as a "can," provides a hermetically sealed enclosure to house an implantable pulse generator (IPG) comprising signal processing and/or pulse generating circuitry powered by a battery. Housing 20 is typically formed of a conductive biocompatible metal, such as titanium, or a non-conductive biocompatible polymeric or ceramic material.

Axial lead connector assembly 22 comprises a connector header formed of, for example, an injection molded dielectric material such as polyurethane. Connector module assembly 22 defines an elongated axial lead bore 30 to receive a proximal end 24 of lead 14. A distal end 25 of lead 14 includes a plurality of electrodes 29, and the proximal end 24 of lead 14 includes a plurality of lead contacts 26A, 26B, 26C, 26D (collectively contacts 26). Lead contacts 26 may be ring contacts. Electrodes 29 may provide stimulation to tissue of patient 14 to alleviate a variety of symptoms or disorders, as discussed above, or support electrical sensing. Electrical conductors (not shown) with the body of lead 14 couple electrodes 29 to respective contacts 26. Electrical feedthrough conductors extend through housing 20 and couple the electronic circuitry within housing 20 of the IMD 12 with one or more electrical connector elements within axial lead connector assembly 22. The electrical feedthrough conductors may be electrically conductive wires, ribbons, or the like. The electrical connector elements within connector assembly 22 electrically and mechanically engage the lead contacts 26.

Connector module assembly 22 is configured to accommodate a lead 14 with an inline configuration, as shown in FIG. 2, in which a plurality of electrical contacts 26 are positioned axially along the length of the lead. In the example of FIG. 2, a strain relief member 28 is provided within connector assembly 22. Strain relief member 28 allows lead 14 to be mechanically connected to connector module assembly 22 using a locking device, such as a set screw assembly. In some embodiments, a single set screw assembly may be provided, simplifying connection of lead 14 to connector assembly 22. As described in greater detail below, connector assembly 22 incorporates various components, arranged in an axial, in-line stack, that support simple and reliable electrical coupling between lead 14 and circuitry in housing 20 while, in some embodiments, reducing overall size of the connector assembly.

Figure 3:
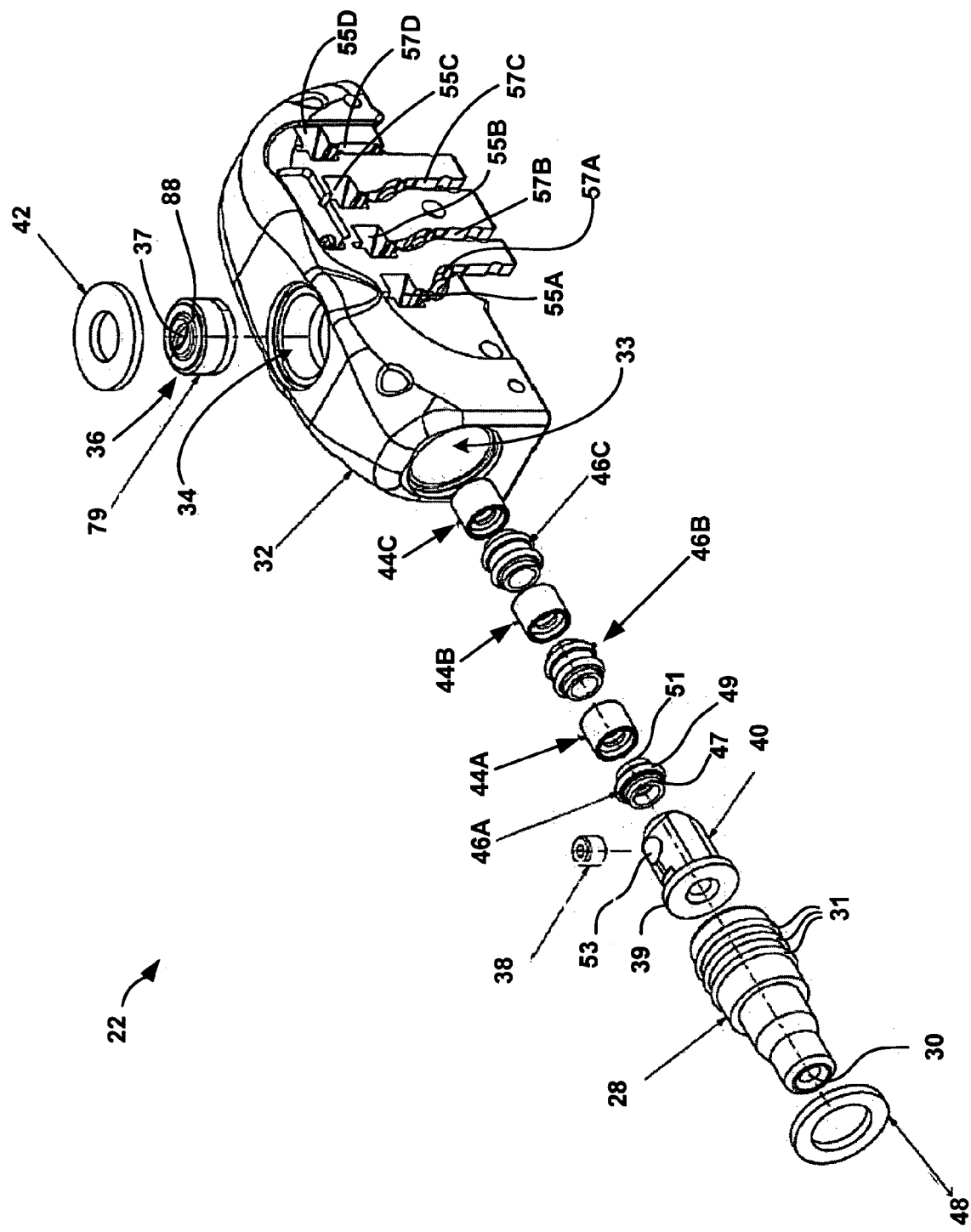
FIG. 3 is an exploded perspective view of an axial lead connector assembly for an IMD.

FIG. 3 is an exploded perspective view of components that form at least a part of axial connector assembly 22 for IMD 12. As shown in FIG. 3, connector header 32 includes a grommet aperture 34 that is disposed substantially perpendicular to an axial stack bore 33 of connector header 32. Axial stack bore 33 receives an axial stack of various components, including strain relief 28, which defines an axial lead bore 30 to receive lead 14. Grommet aperture 34 provides access to axial stack bore 33, and is sized to receive a grommet assembly 36. Grommet assembly 36 is inserted into grommet aperture 34. Grommet assembly 36 includes a compression band 79, e.g., made of silicone, and defines an access aperture 37 that permits a set screw tool to tighten or loosen set screw 38. At least a portion of grommet assembly 36 may be formed from an elastomeric material, such as silicone or polyurethane. When the set screw tightening tool is removed from access aperture 37, grommet assembly 36 closes the access aperture by elastic compression produced by band 36, and thereby self-seals the interior of grommet aperture 34 against bodily fluids. A grommet washer 42 retains grommet assembly 36 in grommet aperture 34.

A stack of alternating, electrical connector elements 44A, 44B, 44C (collectively 44) and annular electrically insulating inner seals 46A, 46B, 46C (collectively 46) is assembled in axial alignment. Each connector element 44 may be integrated with, or adjacent to, a seal 46. In the example of FIG. 3, connector elements 44 and seals 46 are circular. In other embodiments, however, connector elements 44, seals 46 and other connector components may have non-circular cross-sections, such as square, rectangular, oval, or triangular cross-sections. As a further variation, some of connector elements 44 or other connector components may have U-, C- or V-shaped cross sections, in which case lead 14 extends through a trough defined by such cross-section. Inner seals 46 separate adjacent electrical connector elements 44 from one another, and provide a fluid seal between the connector elements.

The stack of connector elements 44 and seals 46 provides an elongated axial lead bore 30 sized in diameter and length to receive lead 14. In particular, each connector component provides a inner passage oriented along a common, longitudinal axis to define axial lead bore 30 to receive lead 14. The position of each connector element 44 corresponds to the position of a respective one of the electrical contacts 26 on lead 14. Each adjacent electrical connector element 44 and inner seal 46 may be interlocked or fitted with one another during preassembly of the stack to maintain axial alignment and length and diameter dimensions. Notably, each connector element 44 can be fitted to at least one adjacent seal 46, without any intervening material from connector header 32. Hence, the distances between adjacent components within the axial stack can be reduced or minimized.

Each electrical connector element 44 may be constructed with an electrically conductive, cylindrical housing having an interior circumferential groove or channel that retains an electrically conductive coil spring element. A distance, or "pitch," between center points of adjacent connector elements 44 may be approximately equal to a pitch between center points of adjacent contacts 26 on lead 14. A spring element in each connector element protrudes slightly into lead bore 30, and is compressed by one of lead contacts 26 when lead 14 is inserted into the lead bore 30. The spring element exerts a spring force against the lead contact 26 to produce enhanced electrical coupling pressure between the spring element and the contact.

For example, each contact 26 of lead 14 may have an outer diameter that is suitably dimensioned to be insertable through the spring element with relatively low force. The spring then provides a radially inward directed spring force on the contact 26. The electrically conductive spring element electrically couples the contact 26 to the electrically conductive outer housing of the connector element 44. Electrical connector elements of the type described above are manufactured by Bal Seal Engineering Company of Foothill Ranch, Calif. In some embodiments, the spring element may be formed from platinum irridium and the housing of the connector element 44 may be formed from MP35N alloy, which is a well known nickel-cobalt-chromium-molybdenum alloy.

Figure 6:
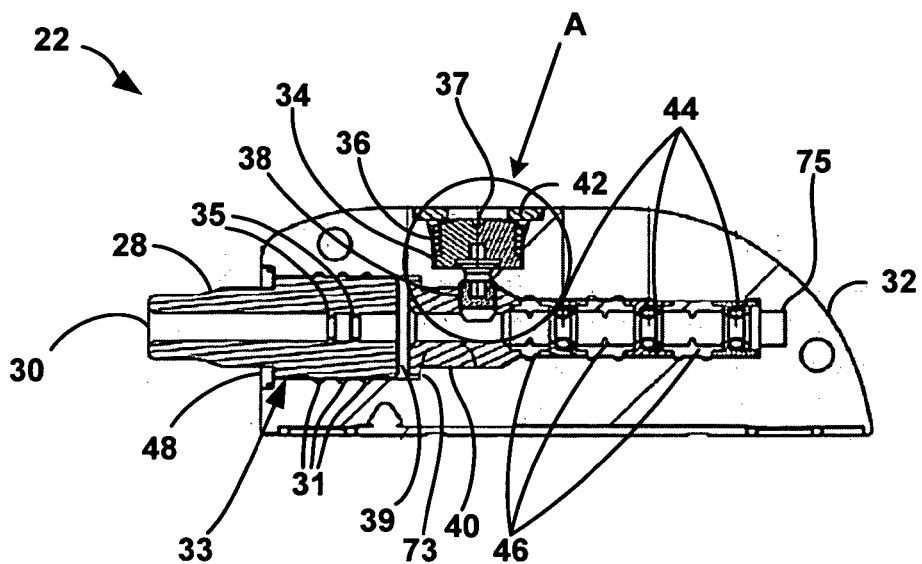
FIG. 6 is a cross-sectional side view of the axial lead connector assembly of FIG. 3.

Inner seals 46 may be formed with one or more annular sealing rings formed in a seal housing. In addition, strain relief member 28 has one or more inner ring seals (not shown in FIG. 3) to seal against lead body 14 and one or more outer ring seals 31 to seal the strain relief member 28 against the bore of connector header 32. The outer ring seals 31 extend radially outward from an outer diameter of strain relief member 28. The inner ring seals associated with strain relief member 28 are shown in FIG. 6. The sealing rings associated with inner seals 46, as shown in FIG. 3, may have an inner diameter slightly smaller than lead bore 30 so that the rings protrude slightly into the bore and are thereby compressed by the outer diameter of lead 14 as the lead slides within the bore. Secure, frictional electrical and mechanical contact is made between lead contacts 26 and electrical connector elements 44, while inner seals 46 seal the electrical connections from fluid ingress that could cause electrical shorting. As mentioned above, a housing of each electrical connector element 44, as well as a spring element carried by the connector element, may be made from MP35N alloy. Alternatively, the spring element may be formed from a different material such as platinum iridium. Seals 46 may be made, for example, from silicone.

The axial stack formed by electrical connector elements 44 and inner seals 46 may further include a locking device, such as set screw assembly 40, located at one end of the stack, as well as strain relief 28. This axial stack may be preassembled or fitted together as a unitary stack, and then inserted a unitary stack into axial stack bore 33 of connector header 32. Alternatively, the components of the axial stack may be inserted in series one after the other, or in groups, according to their order of placement within axial stack bore 33. In either case, there is no need to overmold the connector header over the components of the stack, or consume header space between components. Instead, the components can be stacked one after the other, with no header material separating the components, promoting size reduction.

In addition, there is no need to insert the components of the axial stack laterally into header 32. Instead, all components can be axially inserted through a single entry hole defined by axial stack bore 33, and then staked in placed by a strain relief washer 48, as will be described. In some embodiments, header 32 may be constructed such that there are no apertures to permit lateral insertion of the components of the axial stack. The inner diameter of axial stack bore 33 may vary along its length. In addition, the cross-section of axial stack bore 33, perpendicular to bore length, may not be circular along its entire length.

Set screw assembly 40 may be a single set screw assembly. In other embodiments, two or more set screw assemblies may be provided. However, a single set screw assembly 40 offers reduced complexity and ease of connection of lead 14 to connector assembly 22. Set screw assembly 40 has a connector element bore that is axially aligned with and part of the lead bore 30 and receives inner seal 46A. Inner seal 46A includes a proximal lip 47 that is received by the bore of set screw assembly 40, a ridge 49 and a distal lip 51 that is received by seal 44A. Inner seals 46B and 46C are similarly arranged. However, inner seals 46B and 46C may have a longer axial length than seal 44A, and include an additional ridge.

Set screw assembly 40 also has a set screw bore 53 that is transverse to the connector element bore and contains a set screw 38 adapted to be tightened against a segment of the body of lead 14 within the connector element bore. Before the axial stack of connector components is inserted into connector header 32, set screw 38 may be positioned in set screw assembly 40 by turning clockwise downward until set screw 38 is fully embedded within set screw assembly 40. After the stack is inserted into connector header 32, set screw 38 may be repositioned by backing set screw 38 counterclockwise to a given point. In this manner, the connector element bore within set screw assembly 40 is open to receive lead 14. The set screw 38 may be tightened downward to exert a lateral locking force against a contact 26A carried by lead 14.

Set screw assembly 40 may include a flange 39 that abuts with a stop surface within axial stack bore 33 of connector header 32 to properly position the set screw assembly 40 with respect to grommet aperture 34 in the connector header 32. Set screw assembly 40 is positioned for access via a window 55A. Set screw 38 and set screw assembly 40 may be made from an electrically conductive material such as, for example, titanium. Set screw assembly 40 electrically conducts electrical stimulation or sensed potentials between electrical contact 26A and an electrical conductor, such as a wire, within channel 57A, which communicates with window 55A. Window 55A provides access to couple set screw assembly 40 and a feedthrough conductor, e.g., a wire, within channel 57A, e.g., by welding. As an alternative to set screw assembly 40, other types of locking devices may be provided. As an example, a cam mechanism alternatively may be provided in which a cam is rotated to extend into lead bore 30 to exert pressure against lead 14.

The axial connector stack may further comprise strain relief member 28, which is coaxially aligned with stack bore 33 and lead bore 30. Strain relief member 28 may stabilize the proximal portion of lead 14 inserted within lead bore 30, thereby preventing stretching, bending or twisting due to forces applied to the portion of lead 14 remaining outside lead bore 30. Strain relief member 28 may be made from silicone or other suitable materials. A strain relief washer 48 is located at one end of the stack. Strain relief washer 48 may be ultrasonically welded to connector header 32, thereby staking strain relief member 28 to the connector header 32 and sealing the junction of lead 14 and lead bore 30 without medical adhesive. Strain relief washer 48 may be made, for example, from polyurethane. As discussed previously, strain relief member 28 includes outer ring seals 31 to seal the strain relief member 28 against the interior of the bore of connector header 32. In addition, strain relief member 28 includes inner ring seals 35 (FIG. 6) that seal against the outer diameter of lead 14. Accordingly, upon insertion, lead 14 must have a sufficient insertion force to overcome interference forces presented by inner ring seals 35, connector elements 44, and inner ring seals 46.

Each electrical connector element 44, inner seal 46, set screw assembly 40, and strain relief member 28 has a predetermined axial length between proximal and distal ends thereof, and the combined axial lengths of the total number of electrical connector elements 44, inner seals 46, set screw assembly 40, and strain relief member 28 define the stack length. The stack can be inserted as a unit, or sequentially one after the other or in groups, into lead bore 30 of connector header 32. When the stack assembly is completed, the stack is fitted into the axial stack bore 33 of connector header 32.

When the fitting assembly is complete, electrical connector elements 44A, 44B and 44C are positioned within lateral windows 55B, 55B, 55D, respectively, for connection with feedthrough wires extending within channels 57B, 57C and 57D, respectively, for electrical connection to circuitry within IMD housing 20. Windows 55A, 55B, 55C provide access to electrically connect connector elements 44A, 44B, 44C to wires within respective channels 57B, 57C, 57D, e.g., by welding.

Upon insertion of lead 14, contacts 26B, 26C, 26D reside within connector elements 44A, 44B and 44C of the axial stack. Contact 26A is not received within a connector element. Instead, contact 26A is received at a position within set screw assembly 40. Set screw 38 then biases contact 26A downward to hold lead 14 in place and promote electrical contact between contact 26A and the electrically conductive set screw assembly 40. Hence, lead 14 includes N electrically conductive contacts, but there are only N−1 connector elements 44A, 44B and 44C disposed at positions corresponding to the N−1 most proximal contacts 26B, 26C, 26D. The screw assembly 40 is positioned such that the set screw 38 exerts a lateral force against the most distal contact carried at the proximal end of the lead 14, i.e., contact 26A.

In operation, a physician inserts the proximal end 24 of lead 14 into lead bore 30 with sufficient force to overcome the insertion forces presented by the springs within connector elements 44A, 44B and 44C and the frictional forces presented by the inner diameters of inner seals 46A, 46B and 46C. The proximal end 24 of lead 14 passes through strain relief member 28 and extends into lead bore 30 so that lead contacts 26 carried by proximal end 24 are brought into alignment with respective connector elements 44 and feedthrough channels 57, which creates an electrical interconnection.

As will be described in further detail below with respect to FIGS. 6 and 7, grommet assembly 36 is disposed within grommet aperture 34. Grommet assembly 36 defines an access aperture 37 to enable rotation of the set screw 38 within grommet aperture 34. In particular, a tool such as a torque wrench or hex wrench may be inserted into access aperture 37 to tighten set screw 38 against or to loosen set screw 38 from a lead contact 26 of lead 14 received in lead bore 30. Tightening set screw 38 may exert a lateral force against the lead 14 such that the proximal end 24 of the lead 14 resists axial displacement under axial loading forces, and may further inhibit retraction of lead 14 from lead bore 30. A grommet washer 42 retains grommet assembly 36 within grommet aperture 34. Grommet washer 42 may be made from polyurethane.

Electrical conductors or feedthrough conductors, e.g., such as an array of preformed niobium ribbons, connected at one end to circuitry within housing 20, are inserted into feedthrough channels 57 of connector header 32. The free ends of the electrical conductors may be welded, e.g., by parallel gap welding, to electrical connector elements 44A, 44B, 44C of the stack for connection with contacts 26B, 26C, 26D, respectively, and to a set screw assembly 40 for connection with contact 26A. The electrical conductors in feedthrough channels 57 connect electrical connector elements 44 and set screw assembly 40 to circuitry of the IMD housed within housing 20. The portion of the axial stack exposed by windows 55 may be over-molded with an elastomeric compound, e.g., silicone or silicone adhesive or other polymers, to fill the remaining space of axial stack bore 33 and present a finished outer surface.

The arrangement components illustrated in FIG. 3 can provide a number of advantages. For example, because a connector housing wall is not required between each electrical connector 44 and inner seal 46, successive electrical connectors 44 can be placed close to one another. In other words, the pitch or "spacing" between adjacent lead contacts 26 disposed axially along the lead tip can be reduced, permitting an increased density of electrical interconnections. Accordingly, this feature is particularly useful for in-line lead systems in which medical lead 14 includes a number of electrical lead contacts disposed along axial positions of the lead. Although four electrical contacts 26 are shown in the figures, the axial stack described herein may be particularly useful with leads carrying greater numbers of contacts, such as eight or sixteen contacts.

Figure 4:
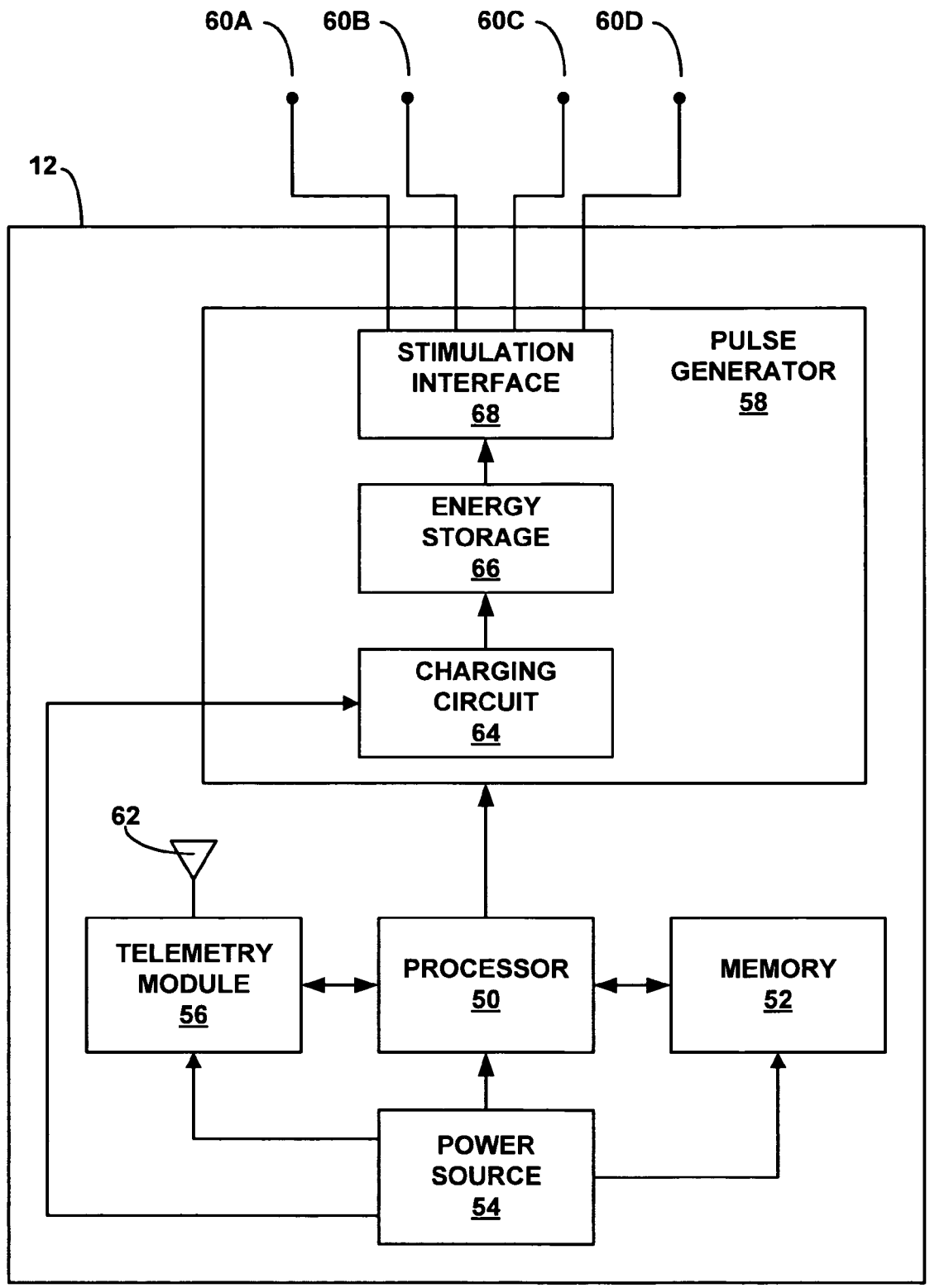
FIG. 4 is a block diagram illustrating exemplary functional components of an IMD.

FIG. 4 is a block diagram illustrating exemplary functional components of IMD 12. In the example of FIG. 4, IMD 12 may include a processor 50, memory 52, power source 54, telemetry module 56, pulse generator 58 and electrodes 60A-60D. Telemetry module 56 is optional and may permit communication with an external controller for transfer of data and adjustment of stimulation parameters. Processor 50 controls operation of IMD 12 and may include one or more microprocessors, digital signal processors (DSPs), application-specific integrated circuits (ASICs), field-programmable gate arrays (FPGAs), or other digital logic circuitry.

Memory 52 may include any magnetic, electronic, or optical media, such as random access memory (RAM), read-only memory (ROM), electronically-erasable programmable ROM (EEPROM), flash memory, or the like. Memory 52 may store program instructions that, when executed by processor 50, cause the processor to perform various functions to support delivery of electrical stimulation, processing of sensed signals or telemetry. For example, memory 52 may store instructions for processor 50 to execute in support of control of telemetry module 56 and pulse generator 58.

Telemetry module 56 may include a transmitter and receiver to permit bi-directional communication between IMD 12 and an external controller. In this manner, external controller 24 may transmit commands to IMD 12 and receive status and operational information from the stimulation device. Telemetry module 56 includes an antenna 62, which may take a variety of forms. For example, antenna 62 may be formed by a conductive coil or wire embedded in a housing 20 associated with IMD 12. Alternatively, antenna 62 may be mounted on a circuit board carrying other components of IMD 12, or take the form of a circuit trace on the circuit board. If IMD 12 does not include a telemetry module 56, a magnetic reed switch may be provided in a circuit between power source 54 and the other components of the device so that, with the aid of an external magnet, the device may be turned on at the time the device is placed in the patient. Alternatively, IMD 12 may simply be activated upon release from an endoscopic delivery device.

Power source 54 may take the form of a battery and power circuitry. The battery may be a non-rechargeable, e.g., primary, battery. The battery may take the form of any of a variety of lithium-ion batteries well known in the implantable medical device arts. Different types of batteries or different battery sizes may be used, depending on the requirements of a given application. In further embodiments, power source 54 may be rechargeable via induction or ultrasonic energy transmission, and include an appropriate circuit for recovering transcutaneously received energy. For example, power source 54 may include a secondary coil and a rectifier circuit for inductive energy transfer. In still other embodiments, power source 54 may not include any storage element, and IMD 12 may be fully powered via transcutaneous inductive energy transfer.

Pulse generator 58 produces an electrical stimulation pulses with parameters, such as voltage or current amplitude, pulse width, pulse rate, and duty cycle, selected to alleviate particular symptoms or provide particular therapy. As shown in FIG. 4, pulse generator 58 includes a charging circuit 64, an energy storage device 66, and a stimulation interface 68. Charging circuit 64 converts energy supplied by power source 54 to charge energy storage device 66, which may be a capacitor. Stimulation interface 68 amplifies and conditions charge from energy storage device 66 to produce an electrical stimulation waveform for application to electrodes 60A-60D, which are carried by a lead such as lead 14. As an example, pulse generator 58 may incorporate circuitry similar to the pulse generation circuitry in the ITREL 3 neurostimulator, commercially available from Medtronic, Inc. of Minneapolis, Minn.

Figure 5:
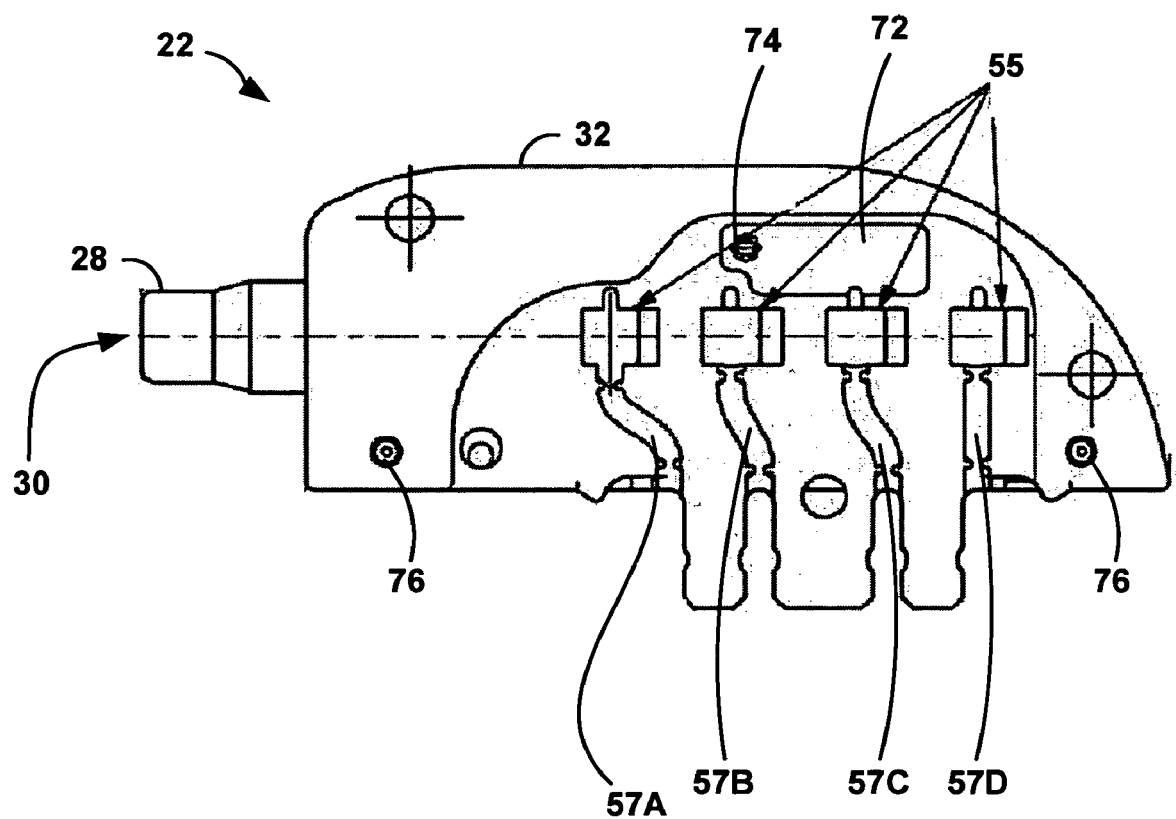
FIG. 5 is a side view of the axial lead connector assembly of FIG. 3.

FIG. 5 is a side view illustrating connector assembly 22 in greater detail. As shown in FIG. 5, feedthrough channels 57 and windows 55 are formed in one side of connector header 32. Electrical feedthrough conductors (not shown) are inserted into feedthrough channels 57 of connector header 32. The free ends of the electrical conductors may be parallel-gap welded to electrical connector elements 44 and set screw assembly 40 within connector module assembly 22 via windows 55. Windows 55 allow manufacturing operators to view the welding process, and may include one or more ramped or chamfered surfaces that taper outward from a narrower space at an internal weld point to the larger weld window. With a chamfer, the internal weld point may be more visible and accessible. A chamfered surface is illustrated in more detail in FIG. 8.

Connector header 32 may further include a cavity 72 for receiving a radio-opaque identifier tag (not shown) for identification of the IMD, e.g., by model number, serial number, stimulation or sensing capabilities, or the like. In the example of FIG. 5, cavity 72 includes a fastening hole 74 for fastening the radio-opaque identifier tag to cavity 72. Connector header 32 also includes holes 76 formed at a base of connector header 32 for attaching connector assembly 22 to housing 20, as will be discussed in further detail with respect to FIG. 12. In general, after attachment of connector assembly 22 to housing 20, a physician simply inserts lead 14 into axial lead bore 30 defined by the axial stack of components, and tightens set screw 38 to hold the proximal end of lead 14 in place within the connector assembly.

FIG. 6 is a cross-sectional side view of connector module assembly 22 of FIG. 5. As shown in FIG. 6, grommet assembly 36 is disposed within grommet aperture 34 to enable insertion of a tool, such as a torque wrench or hex wrench, for rotation of set screw 38. The tool is inserted via access aperture 37 and serves to tighten set screw 38 against or to loosen set screw 38 from contact 26A of lead 14 received in lead bore 30 of set screw assembly 40. Grommet assembly 36 is retained within connector header 32 by grommet washer 42. Set screw assembly 40 may include a flange 39 that abuts a stop 73 within the interior axial stack bore 33 of connector header 32. Stop 73 may be molded into connector header 32. Stop 73 and flange 39 serve to properly position set screw 38 and set screw assembly 40 with respect to grommet aperture 34 in connector header 32, and with respect to window 55A for connection of the electrically conductive set screw assembly 40 to a feedthrough wire within channel 57A.

When the in-line stack comprising electrical connector elements 44, inner seals 46, set screw assembly 40, and strain relief 28 is inserted into axial stack bore 33 of connector header 32, flange 39 abuts stop 73, thereby preventing the stack from being inserted beyond a certain point into axial stack bore 33. In this manner, set screw 38 is properly aligned with grommet aperture 34 within connector header 32 and, more particularly, access aperture 37 in grommet assembly 36. Strain relief washer 48 is then ultrasonically welded to connector header 32 at the opening of recess 45 to seal the stack within connector header 32.

As shown in FIG. 6, strain relief 28 further includes inner ring seal members 35 which protrude into lead bore 30 for interference with lead 14. Inner ring seal members 35 provide a substantial fluid seal against lead 14, while outer ring seal members 31 provides a substantial fluid seal against the interior axial stack bore 33 of connector header 32. Strain relief 28, including seals 31 and seals 35, may be integrally molded, e.g., from silicone. Upon implantation, the proximal end of lead 14 is inserted up to the point that the proximal end abuts a stop 75 within connector header 32, at which point contact 26A is aligned with set screw assembly 40 and contacts 26B, 26C, 26D are aligned with respective connector elements 44A, 44B, 44C.

Portion A of FIG. 6 illustrates components within grommet aperture 34 of connector header 32. Portion A is enlarged and illustrated in further detail in FIG. 7. In particular, FIG. 7 is a cross-sectional side view of grommet assembly 36 and set screw 38. Grommet assembly 36 provides an access aperture 37 that permits access of a set screw tightening device to engage a socket 80 of set screw 38 for enabling rotation of set screw 38 within set screw assembly 40. FIG. 8 is a cross-sectional front view of grommet assembly 36 of FIG. 7.

Socket 80 may be a slot, a star, a hexagon, or any other shape. A main body of set screw 38 is threaded for engagement with a threaded set screw bore 53. At implantation, the proximal end 24 of lead 14 is inserted into lead bore 30 of connector module 22 to locate contact 26A within set screw assembly 40. A set screw tightening tool, e.g., a hex wrench or torque wrench, may be inserted through grommet washer 42 and grommet assembly 36 into access aperture 37 to engage a socket in set screw 38. By rotating the tightening tool, set screw 38 tightens against an inner surface of set screw assembly 40 and ensures electrical contact between contact 26A of lead 14 and the circuitry within housing 20, via the electrically conductive set screw assembly 40 and the feedthrough wire within channel 57A.

In some embodiments, grommet assembly 36 may be formed from silicone, polyurethane or other soft elastomeric material. In the example of FIGS. 6-8, grommet assembly is formed from a first half grommet 77A and a second half grommet 77B, which are held together by a ring-like, compressive band 79 that extends around a periphery of the half grommets 77A, 77B. An interface 88 between the half grommets 77A, 77B defines the access aperture 37, which is normally closed due to the compressive bias applied by band 79. Band 79 may be formed from an elastomeric material, such as silicone. With the compressive force applied by band 79, access aperture 37 forms a self-sealing slit through which a tool can be inserted to access set screw 38.

A ring of adhesive may be provided around a top surface of grommet assembly 36. Outer, lower surfaces of grommet assembly 36 seal against a lower, smaller diameter portion of grommet 34 aperture, eliminating the need for the adhesive. For example, grommet aperture 34 may include a shelf and smaller diameter portion near the bottom of the aperture that compresses and seals against a bottom portion 82 of grommet assembly 36, which may be more flexible. The sealing pressure between the bottom portion 82 of grommet assembly and the reduced diameter wall of grommet aperture 34 may result in less "push-back" of grommet assembly 36 against grommet aperture 34, which may reduce relaxation of the material forming connector header 32 and subsequent reduction in sealing performance.

Figure 7:
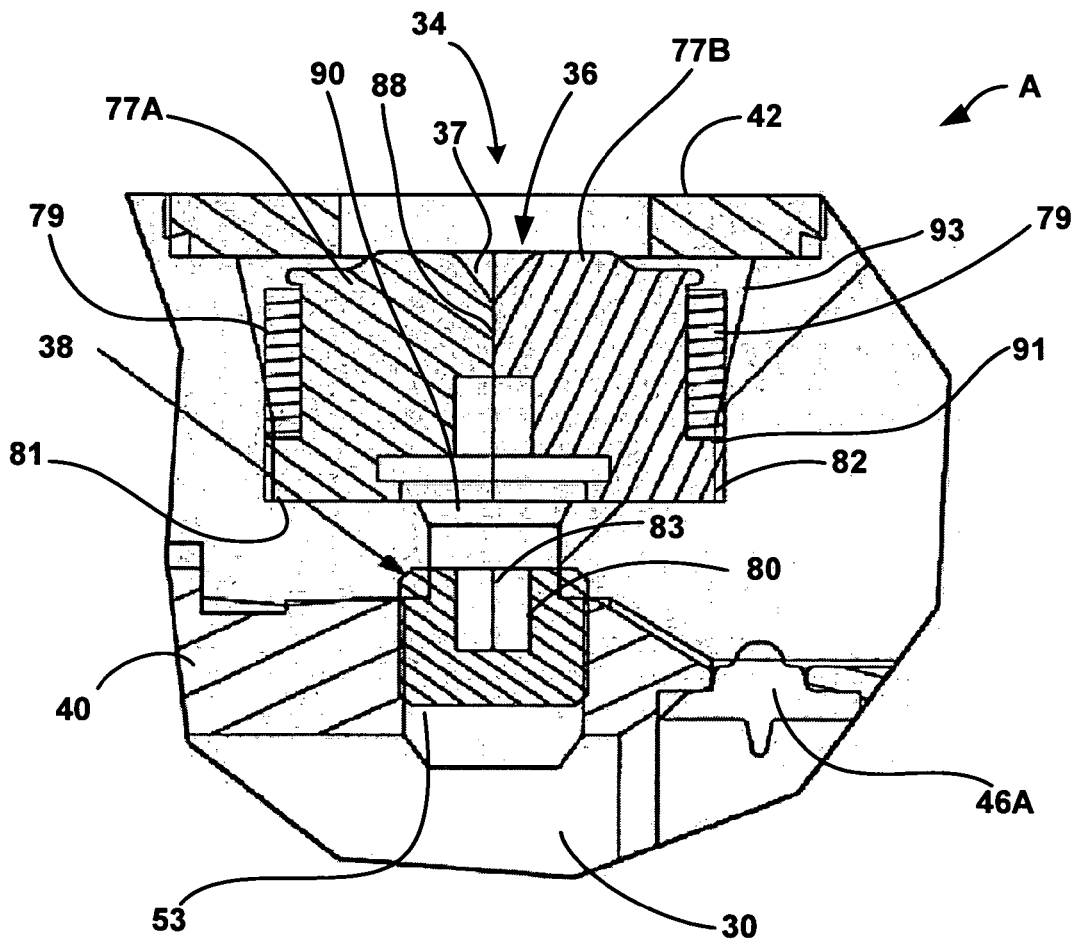
FIG. 7 is an enlarged cross-sectional side view of a locking device in the axial lead connector assembly of FIG. 3.
Figure 8:
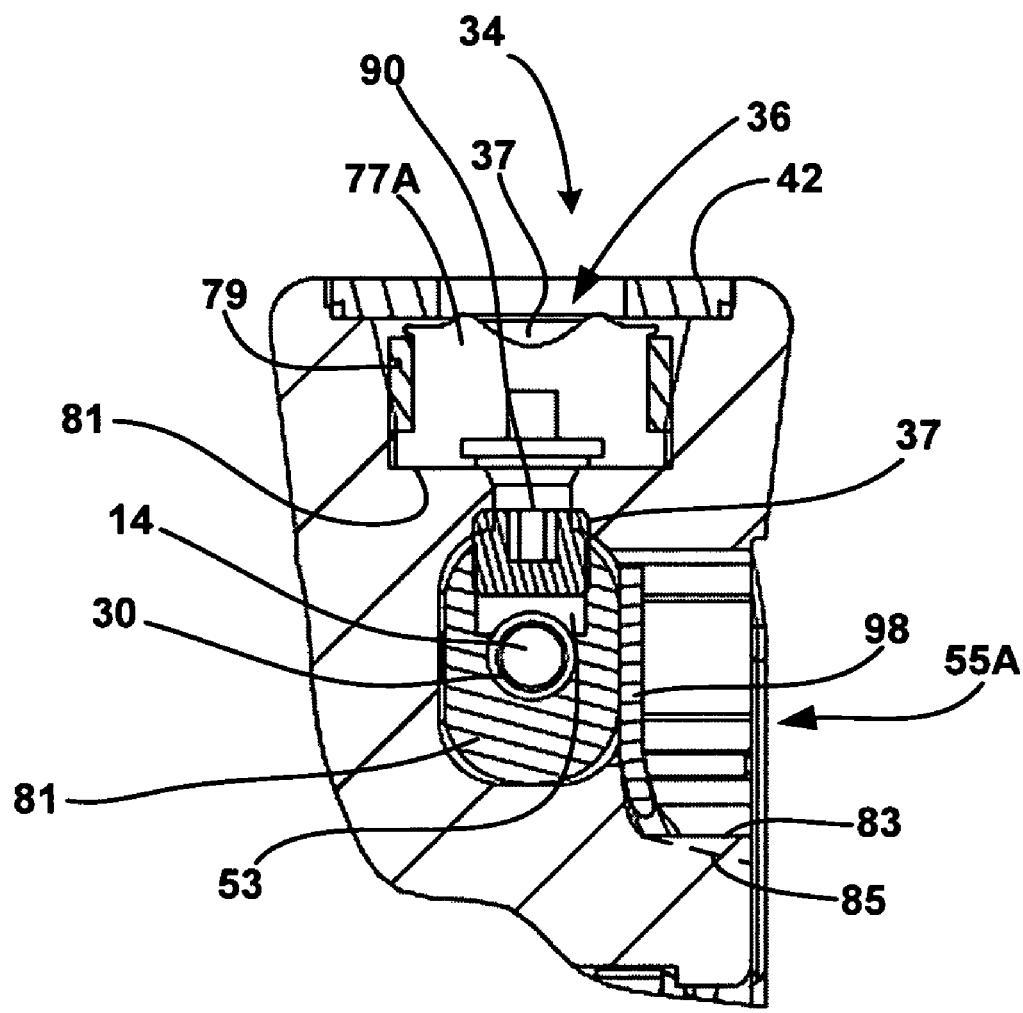
FIG. 8 is a cross-sectional front view of the locking device of FIG. 7.

In some embodiments, as shown in FIG. 7, grommet aperture 34 may include a tapered diameter or conical shape such that the inner sealing surfaces of the grommet assembly 36 at interface 88 are minimally compressed by the grommet aperture 34, which may reduce permanent sealing of the sealing surfaces and possible damage and reduced sealing performance after tool insertion and removal. For example, grommet aperture 34 may include a smaller diameter section 91 at the bottom of the aperture and a larger diameter section 93 that tapers from the smaller diameter adjacent small diameter section 91 to a larger diameter near grommet washer 42. As also shown in FIG. 7, an outer diameter of grommet assembly 36 is larger than an inner diameter of washer 42, thereby serving to retain the grommet assembly within connector head 32. Also, the outer diameter of set screw 38 may be larger than an inner diameter of the channel 90 between set screw 38 and grommet assembly 36. The shape of grommet aperture 34 and channel 90 is further sized such that a wrench may access socket 80 of set screw 38, but set screw 38 cannot be backed out into grommet aperture 34. This may eliminate set screw 38 from "wandering" out of set screw assembly 40.

FIG. 8 provides a cross-sectional front view of connector header 32, from a direction looking into axial lead bore 30. FIG. 8 further illustrates a chamfered surface 85 within windows 57. Window 57A, for example, has a generally flat surface 83 that extends outward from a weld point between set screw assembly 40 and a feedthrough conductor 98. In some embodiments, however, a chamfered surface 85 may be provided, as illustrated in dashed lines. The chamfered surface 85 ramps downward in a tapered manner from a narrower space proximate the weld point to a larger space that defines the weld window for access by a technician. In this manner, the cross-sectional surface area in a direction looking into window 57A increases from a smaller cross-sectional surface area proximate the weld point between conductor 98 and set screw assembly 40 to a larger cross-section surface area at the outer entrance of the window. With a chamfered surface 85, the internal weld point may be more visible and accessible. One of more surfaces defining window 57 may be chamfered. For example, window 57 may be chamfered on one side, two sides, or all sides. In addition, each of windows 57A-57D may include at least one chamfered surface 81.

Figure 9:
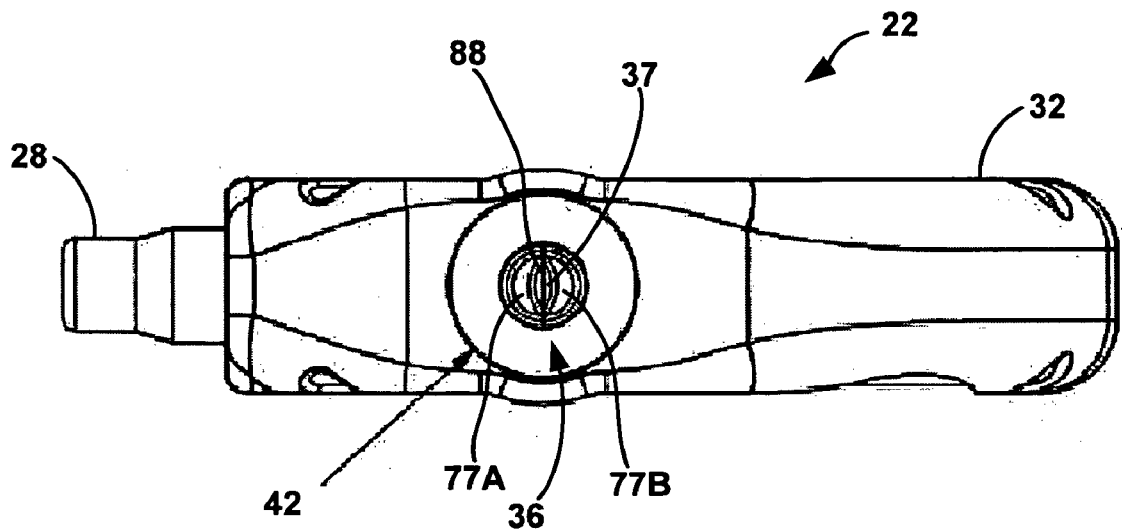
FIG. 9 is a top view of the axial lead connector assembly of FIG. 3.

FIG. 9 is a top view of connector module assembly 22. As shown in FIG. 9, the top of half grommets 77A, 77B and the access aperture 37 formed by the interface between the half-grommets can be viewed through an opening of grommet washer 42. A tightening tool, e.g., a torque wrench or a hex wrench, may be inserted through access aperture 37 of grommet assembly 36 to rotate and tighten set screw 38 against a lead contact 26 of lead 14.

Figure 10:
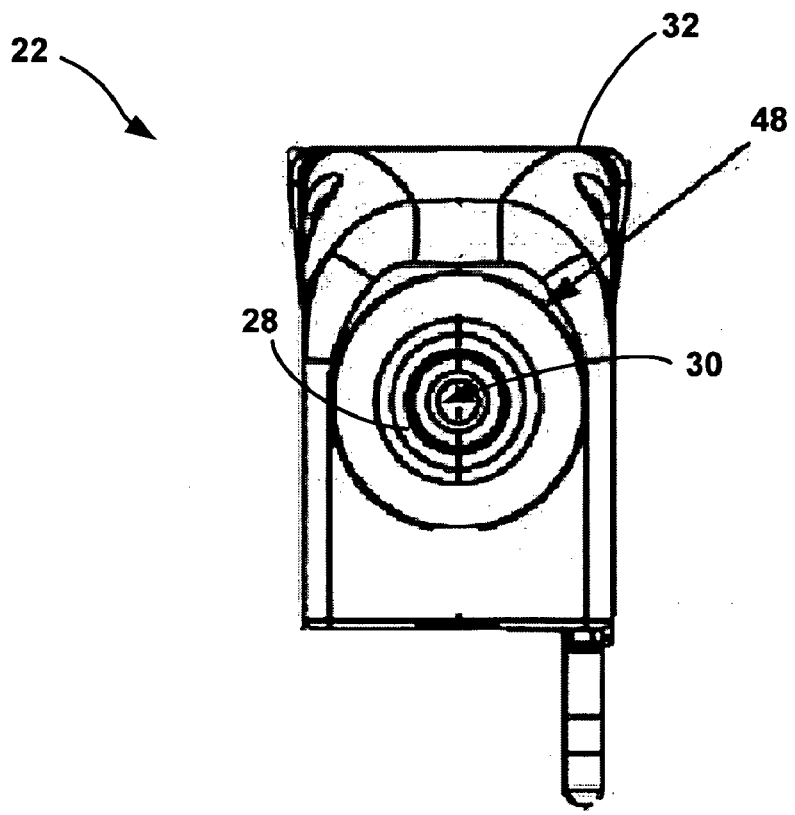
FIG. 10 is a front view of the axial lead connector assembly of FIG. 3.
Figure 11:
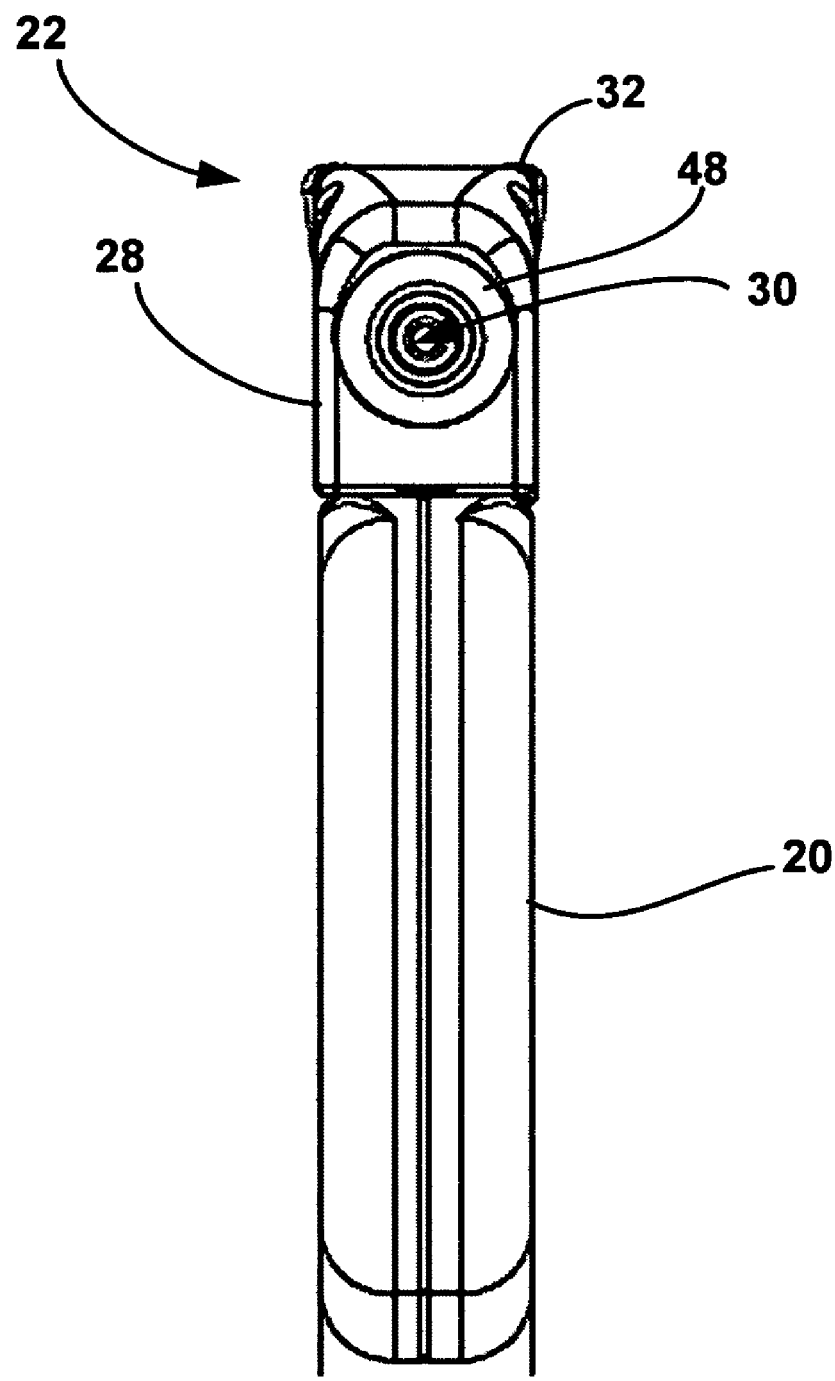
FIG. 11 is a front view of the axial lead connector assembly of FIG. 3 and an IMD housing.

FIG. 10 is a front view of connector module assembly 22. FIG. 11 is a front view of lead connector assembly 22 and the IMD housing 20. As can be seen from FIGS. 9-11, a portion of strain relief member 28 extends outside of connector header 32. Strain relief washer 48 has an inner diameter that is smaller than a diameter of a portion of strain relief member 28 within axial stack bore 33, thereby retaining strain relief 28 within connector header 32. In particular, strain relief washer 48 may be ultrasonically welded to connector header 32 to hold the stack containing strain relief member 28 in place within connector header 32. Strain relief washer 48 seals the portion of strain relief member 28 having a larger diameter than strain relief washer 48 within axial stack bore 33 of connector header 32. Also shown in FIGS. 10 and 11 is axial lead bore 30, where lead 14 may be inserted into connector module assembly 22.

Figure 12:
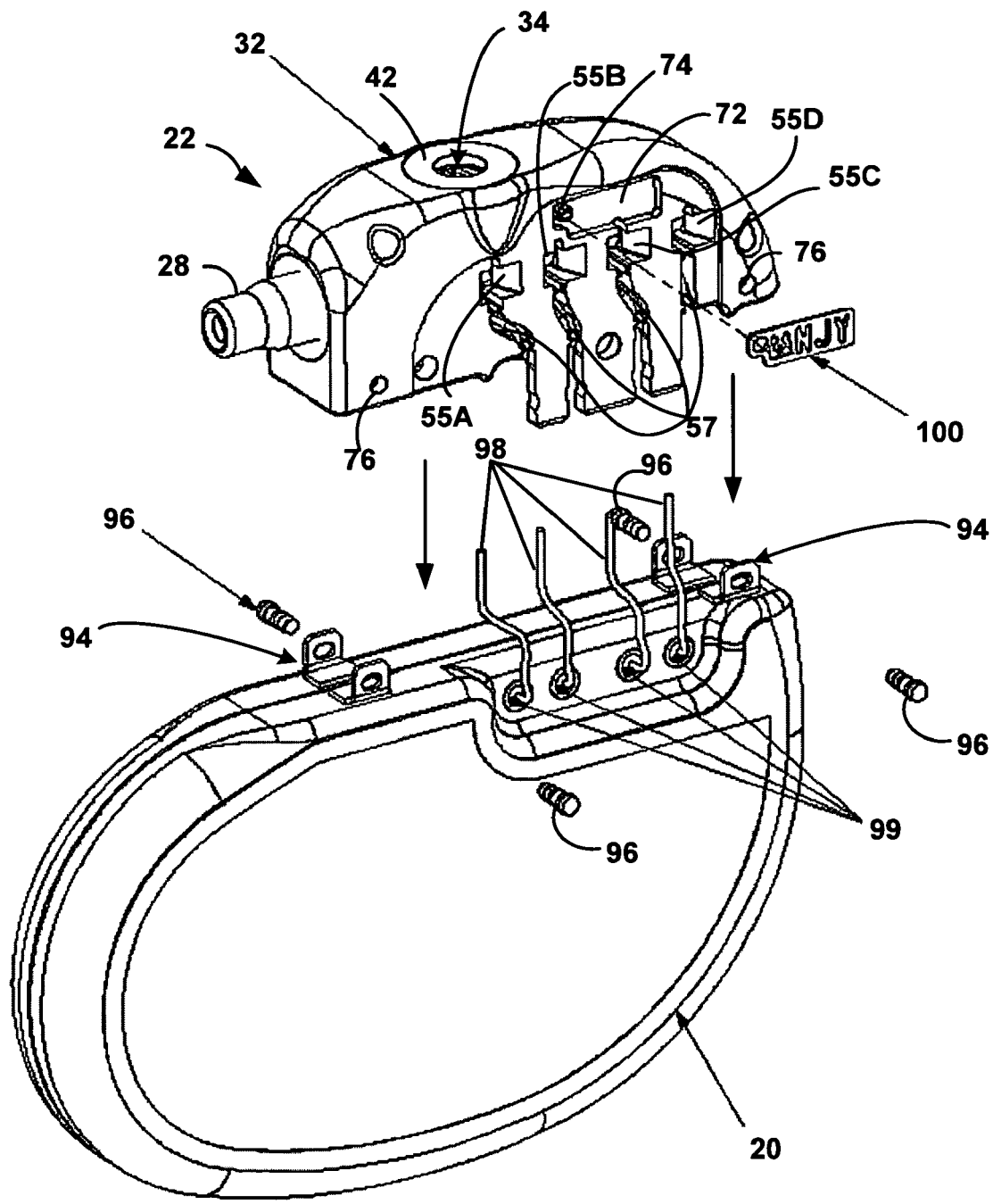
FIG. 12 is an exploded perspective view of the axial lead connector assembly and the IMD housing.

FIG. 12 is an exploded perspective view of connector module assembly 22 and housing 20. Connector module assembly 22 is connected to housing 20 by a pin and strap mechanism. In particular, four holes 76 are formed at the base of connector header 32 (only two of which are visible in FIG. 12). Connector module assembly 22 is placed upon housing 20 such that holes 76 align with straps 94 of housing 20. Pins 96 are inserted through straps 94 and into holes 76 to secure connector module assembly 22 to housing 20. An adhesive may additionally be used to secure connector module assembly 22 to housing 20. Such an adhesive may provide mechanical strength to the connection between connector module assembly 22 and housing 20, and also may provide a barrier preventing fluid ingress to the area between connector module assembly 22 and housing 20.

Electrical feedthrough wires 98 are connected inside housing 20 to electronic circuitry of an IPG within housing 20. Ferrules 99 are present where electrical feedthrough wires 98 emerge from housing 20. The point at which electrical feedthrough wires 98 emerge from housing 20 may be filled with encapsulant. When connector module assembly 22 is secured to housing 20, electrical feedthrough wires 98 are inserted into feedthrough channels 57 of connector header 32. The free ends of electrical feedthrough wires 98 are parallel-gap welded to electrical connector elements 44 and set screw assembly 40, as applicable, within connector module assembly 22.

Connector header 32 has a cavity 72 formed therein for receiving radio-opaque identifier tag 100. Cavity 72 includes a fastening hole 74 for fastening radio-opaque identifier tag 100 to radio-opaque cavity 72. Radio-opaque identifier tag 100 may have a code for identification of the IMD. Radio-opaque identifier tag 100 may be made of a radio-opaque metal, e.g., tungsten.

An elastomeric compound, e.g., silicone rubber or silicone adhesive or other polymers, is injected within connector module assembly 22 to fill the remaining space of axial stack bore 33 and present a finished outer surface. The elastomeric compound is injected until the elastomeric compound is visible flowing out of feedthrough channels 57. Radio-opaque identifier tag 100 may be readable through the adhesive via X-ray.

Although described for purposes of illustration as having four lead contacts 26 and four corresponding electrical terminals in the form of connector elements 44 and set screw assembly 40, the invention may be implemented with a different amount of lead contacts and electrical connection elements, e.g., eight. The eight lead contacts and electrical connection elements may be located axially in-line, or connector header 32 may include two bores, e.g., with four axially aligned contacts each. To overcome the increased frictional force associated with an increased number of electrical connection elements disposed axially within connector header 32, lead 14 may be a variable diameter lead. In particular, lead 14 may taper from a narrower diameter at the proximal tip to a larger diameter at a position away from the proximal tip, e.g., coincident with electrical contact 26A.

The dimensions of the various components described herein may vary according to different applications or design considerations. The following dimensions are exemplary and should not be considered limiting of the invention as broadly embodied and described herein. In an exemplary embodiment, lead 14 may have an outer diameter of approximately 1 mm to 2 mm, strain relief washer 48 may have an inner diameter of approximately 2 mm to 5 mm, strain relief 28 may have an inner diameter of approximately 1 mm to 2 mm and an outer diameter of approximately 3.5 mm to 6 mm. However, a portion of strain relief 28 passing through strain relief washer 48 will have an outer diameter slightly smaller than the inner diameter of the strain relief washer. Outer ring seals 31 may define approximately an additional 0.25 mm to 1 mm beyond the outer diameter of the strain relief, and inner ring seals 35 may define approximately an additional 0.25 mm to 1 mm beyond the inner diameter of the strain relief. The inner diameter of strain relief 28 generally defines the diameter of axial lead bore 30, and is substantially common among the stack components.

Grommet washer 42 may have an inner diameter of approximately 2 mm to 4 mm, and grommet assembly 36 may have an outer diameter of approximately 4 mm to 5 mm. Grommet aperture 34 may have a minimum diameter of approximately 3.5 mm to 4.5 mm, a maximum diameter of approximately 4.5 mm to 6 mm (i.e., at the maximum extent of the tapered or conical region), and a depth of approximately 2.5 mm to 4 mm. Electrical connector elements 44 may each have an inner diameter approximately equal to the diameter of axial lead bore 30, and an outer diameter of approximately 2 mm to 4 mm. Inner seals 46 may have an inner diameter slightly smaller than the diameter of axial lead bore 30 and an outer diameter of approximately 2.2 mm to 5 mm. The overall length of the stack of components, e.g., strain relief 28, set screw assembly 40, connector elements 44 and seals 46, along the length of axial lead bore 30, may be in a range of approximately 22 mm to 35 mm.

Various embodiments of the invention have been described. These and other embodiments are within the scope of the following claims.

The invention claimed is:

1. An implantable medical device comprising:
    a connector header defining a first axial bore and comprising a stop surface within the first axial bore; and
    a series of electrical connector elements, fluid seals, and a locking device arranged in an axial stack mounted within the first axial bore,
    wherein the axial stack defines a second axial bore that extends through the electrical connector elements, fluid seals, and the locking device,
    wherein the second axial bore is configured to receive a proximal end of an implantable medical lead,
    wherein the locking device exerts a lateral force against the lead such that the proximal end of the lead substantially resists axial displacement under axial loading forces,
    wherein the locking device is positioned within the axial stack at a position distal to at least one of the electrical connector elements,
    wherein the first axial bore comprises an axial opening that is configured to axially receive the electrical connector elements, fluid seals, and locking device when the electrical connector elements, fluid seal, and locking device are axially inserted,
    wherein the locking device includes a flange that engages the stop surface to position the locking device, and
    wherein the locking device is electrically conductive and is disposed within the second axial bore at a position corresponding to an electrically conductive contact carried by the proximal end of the lead.

2. The device of claim 1, wherein the electrical connector elements are disposed at positions corresponding to electrically conductive contacts carried by the proximal end of the lead, and some of the fluid seals are disposed between adjacent electrically conductive contacts.

3. The device of claim 1, wherein the locking device includes a set screw assembly with a set screw that is rotatable to extend into the second axial bore and exert the lateral force against the lead, wherein the set screw assembly is electrically conductive.

4. The device of claim 3, wherein the lead includes N electrically conductive contacts, the connector elements include N−1 connector elements disposed at positions corresponding to the N−1 most proximal contacts carried at the proximal end of the lead, and the set screw assembly is positioned to exert a lateral force against the most distal electrically conductive contact carried at the proximal end of the lead.

5. The device of claim 3, wherein the set screw assembly is a single set screw assembly.

6. The device of claim 3, further comprising:
a grommet aperture defined within the connector header perpendicular to the first axial bore, wherein the grommet aperture provides access to the first axial bore; and
a grommet assembly within the grommet aperture, wherein the grommet assembly defines a self-sealing access aperture that permits insertion of a tool to tighten the set screw against one of the lead contacts of the lead.

7. The device of claim 6, wherein the grommet aperture has a cross-section with a first diameter sized to compress the grommet assembly, and a second diameter larger than the first diameter.

8. The device of claim 1, further comprising a strain relief member arranged in the axial stack, wherein the second axial bore extends through the strain relief member, and a fixation member coupled to the strain relief member to retain the axial stack within the first axial bore.

9. The device of claim 1, wherein each of the connector elements includes a spring element that exerts an inward force against one of the contacts.

10. The device of claim 1, further comprising a plurality of lateral windows that permit lateral access to the connector elements to couple feedthrough conductors to the connector elements, wherein each of the windows defines at least one chamfered surface.

11. The device of claim 1, wherein adjacent components in the axial stack are in substantially direct contact with one another.

12. An implantable medical device comprising:
a connector header defining a first axial bore and comprising a stop surface within the first axial bore; and
an axial stack of connector components within the first axial bore,
wherein the axial stack defines a second axial bore extending through the components that is configured to receive a proximal end of an implantable medical lead,
wherein the components include electrical connector elements, fluid seals, a locking device that exerts a force to resist displacement of the lead, and a strain relief member,
wherein the locking device is positioned within the axial stack at a position distal to at least one of the electrical connector elements,
wherein the first axial bore comprises an axial opening that is configured to axially receive the axial stack when the axial stack is axially inserted, and
wherein the locking device includes a flange that engages the stop surface to position the locking device.

13. The device of claim 12, wherein the electrical connector elements are disposed at positions corresponding to electrically conductive contacts carried by the proximal end of the lead, and some of the fluid seals are disposed between adjacent electrically conductive contacts.

14. The device of claim 13, wherein the locking device is electrically conductive and is disposed within the second axial bore at a position corresponding to an electrically conductive contact carried by the proximal end of the lead.

15. The device of claim 14, wherein the locking device includes a set screw assembly with a set screw that is rotatable to extend into the second axial bore and exert the lateral force against the lead, wherein the set screw assembly is electrically conductive.

16. The device of claim 15, further comprising:
a grommet aperture defined within the connector header perpendicular to the first axial bore, wherein the grommet aperture provides access to the first axial bore; and
a grommet assembly within the grommet aperture, wherein the grommet assembly defines a self-sealing access aperture that permits insertion of a tool to tighten the set screw against one of the lead contacts of the lead.

17. The device of claim 16, wherein the grommet aperture has a cross-section with a first diameter sized to compress the grommet assembly, and a second diameter larger than the first diameter.

18. The device of claim 12, further comprising a fixation member coupled to the strain relief member to retain the axial stack within the first axial bore.

19. The device of claim 12, further comprising a plurality of lateral windows that permit lateral access to the connector elements to couple feedthrough conductors to the connector elements, wherein each of the windows defines at least one chamfered surface.

20. The device of claim 12, wherein adjacent components in the axial stack are in substantially direct contact with one another.

21. An implantable medical device comprising:
a connector header defining a first axial bore and comprising a stop surface within the first axial bore;
a series of electrical connector elements, fluid seals, a locking device, and a strain relief member arranged in an axial stack mounted within the first axial bore, wherein the axial stack defines a second axial bore that extends through the electrical connector elements, fluid seals, the locking device, and the strain relief member; and
a fixation member coupled to the strain relief member to retain the axial stack within the first axial bore,
wherein the second axial bore is configured to receive a proximal end of an implantable medical lead,
wherein the locking device exerts a lateral force against the lead such that the proximal end of the lead substantially resists axial displacement under axial loading forces,
wherein the locking device is positioned within the axial stack at a position distal to at least one of the electrical connector elements,
wherein the first axial bore comprises an axial opening that is configured to axially receive the electrical connector elements, fluid seals, and locking device, and
wherein the locking device includes a flange that engages the stop surface to position the locking device when the electrical connector elements, fluid seal, and locking device are axially inserted.

22. A method for assembling an electrical connector assembly for an implantable medical device comprising:
arranging a series of electrical connector elements, fluid seals, and a locking device in an axial stack; and
axially inserting the axial stack into a first axial bore defined by a connector header, wherein the axial stack defines a second axial bore that extends through the electrical connector elements, fluid seals, and the locking device to receive a proximal end of an implantable medical lead, wherein axially inserting the axial stack comprises axially inserting the axial stack into the first axial bore such that the locking device is positioned within the axial stack at a position distal to at least one of the electrical connector elements, wherein the locking device is configured to exert a lateral force against the lead such that the proximal end of the lead substantially resists axial displacement under axial loading forces, wherein the locking device includes a flange, wherein axially inserting the axial stack includes axially inserting the axial stack into the first axial bore until the flange engages a stop surface of the connector header to position the locking device, wherein the locking device includes a set screw assembly with a set screw that is rotatable to extend into the second axial bore and exert the lateral force against the lead, and wherein the set screw assembly is electrically conductive.

23. The method of claim 22, wherein arranging includes arranging the electrical connector elements at positions corresponding to electrically conductive contacts carried by the proximal end of the lead, and arranging some of the fluid seals are disposed between adjacent electrically conductive contacts.

24. The method of claim 23, further comprising attaching the electrical connector elements to feedthrough conductors associated with the implantable medical device via lateral windows, wherein each of the windows defines at least one chamfered surface.

25. The method of claim 23, wherein arranging includes arranging adjacent components in the axial stack so that the components are in substantially direct contact with one another.

26. The method of claim 22, wherein the locking device is electrically conductive, and arranging further includes arranging the locking device in the axial stack at a position corresponding to an electrically conductive contact carried by the proximal end of the lead.

27. The method of claim 22, wherein the lead includes N electrically conductive contacts, and the connector elements include N−1 connector elements disposed at positions corresponding to the N−1 most proximal contacts carried at the proximal end of the lead, and arranging includes arrange the set screw assembly at a position in the lateral stack to exert a lateral force against the most distal electrically conductive contact carried at the proximal end of the lead.

28. The method of claim 22, wherein arranging includes arranging a single set screw assembly in the axial stack.

29. The method of claim 22 further comprising inserting a grommet assembly into a grommet aperture defined within the connector header perpendicular to the first axial bore, wherein the grommet aperture provides access to the first axial bore, and wherein the grommet assembly defines a self-sealing access aperture that permits insertion of a tool to tighten the set screw against one of the lead contacts of the lead.

30. The method of claim 29, wherein the grommet aperture has a cross-section with a first diameter sized to compress the grommet assembly, and a second diameter larger than the first diameter.

31. The method of claim 22, further comprising inserting the proximal end of the lead into the second axial bore, and actuating the set screw to lock the lead within the second axial bore.

32. The method of claim 22, wherein arranging further includes arranging a strain relief member in the axial stack, wherein the second axial bore extends through the strain relief member, the method further comprising coupling a fixation member to the strain relief member to retain the axial stack within the first axial bore.

33. A method for assembling an electrical connector assembly for an implantable medical device comprising:

arranging a series of electrical connector elements, fluid seals, and a locking device in an axial stack; and axially inserting the axial stack into a first axial bore defined by a connector header, wherein the axial stack defines a second axial bore that extends through the electrical connector elements, fluid seals, and the locking device to receive a proximal end of an implantable medical lead, wherein axially inserting the axial stack comprises axially inserting the axial stack into the first axial bore such that the locking device is positioned within the axial stack at a position distal to at least one of the electrical connector elements, wherein the locking device is configured to exert a lateral force against the lead such that the proximal end of the lead substantially resists axial displacement under axial loading forces, wherein the locking device includes a flange, wherein axially inserting the axial stack includes axially inserting the axial stack into the first axial bore until the flange engages a stop surface of the connector header to position the locking device, and wherein the locking device is electrically conductive, and arranging further includes arranging the locking device in the axial stack at a position corresponding to an electrically conductive contact carried by the proximal end of the lead.

34. A method for assembling an electrical connector assembly for an implantable medical device comprising:

arranging a series of electrical connector elements, fluid seals, a locking device, and a strain relief member in an axial stack;

axially inserting the axial stack into a first axial bore defined by a connector header; and coupling a fixation member to the strain relief member to retain the axial stack within the first axial bore, wherein the axial stack defines a second axial bore that extends through the electrical connector elements, fluid seals, the locking device, and the strain relief member to receive a proximal end of an implantable medical lead, wherein axially inserting the axial stack comprises axially inserting the axial stack into the first axial bore such that the locking device is positioned within the axial stack at a position distal to at least one of the electrical connector elements, wherein the locking device is configured to exert a lateral force against the lead such that the proximal end of the lead substantially resists axial displacement under axial loading forces, and wherein the locking device includes a flange, wherein axially inserting the axial stack includes axially inserting the axial stack into the first axial bore until the flange engages a stop surface of the connector header to position the locking device.

* * * * *

UNITED STATES PATENT AND TRADEMARK OFFICE
CERTIFICATE OF CORRECTION

| | | |
|---|---|---|
| PATENT NO. | : 7,590,451 B2 | Page 1 of 1 |
| APPLICATION NO. | : 11/263526 | |
| DATED | : September 15, 2009 | |
| INVENTOR(S) | : Carole Tronnes | |

It is certified that error appears in the above-identified patent and that said Letters Patent is hereby corrected as shown below:

Title page, item [73] and Col. 1, line 5
Title
Kindly replace "Axial Lead Connector for Implantable Medical Devices" with -- Axial Lead Connector for Implantable Medical Device --.

Column 16
Line 57, "and locking device, and" should be replaced with -- and locking device, when the electrical connector elements, fluid seal, and locking device are axially inserted, and --.

Lines 58-61, Kindly delete "when the electrical connector elements, fluid seal, and locking device are axially inserted".

Column 17
Line 46, "and arranging includes arrange the" should read -- and arranging includes arranging the --.

Line 52, "The method of claim 22 further" should read -- The method of claim 22, further --.

Signed and Sealed this

Ninth Day of February, 2010

David J. Kappos
*Director of the United States Patent and Trademark Office*

UNITED STATES PATENT AND TRADEMARK OFFICE
CERTIFICATE OF CORRECTION

PATENT NO.        : 7,590,451 B2                                   Page 1 of 1
APPLICATION NO.   : 11/263526
DATED             : September 15, 2009
INVENTOR(S)       : Tronnes et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 734 days.

Signed and Sealed this

Twenty-first Day of September, 2010

David J. Kappos
*Director of the United States Patent and Trademark Office*